United States Patent [19]
Sakai et al.

[11] Patent Number: 5,693,320
[45] Date of Patent: Dec. 2, 1997

[54] (METH)ACRYLOYLOXY SUBSTITUTED ACETYLSALICYLATES AND POLYMERS THEREOF

[75] Inventors: Masamune Sakai, Ichihara; Hiroyuki Ikeda, Tokyo; Noriaki Kaneko, Ichihara; Yutaka Tamura, Kisarazu, all of Japan

[73] Assignee: Ube Industries, Ltd., Ube, Japan

[21] Appl. No.: 614,016

[22] Filed: Mar. 12, 1996

[30] Foreign Application Priority Data

Mar. 17, 1996 [JP] Japan .................................. 7-59036

[51] Int. Cl.$^6$ .................. C08F 20/58; C08F 20/18; C08K 5/01; C07C 229/00
[52] U.S. Cl. .................. 424/78.35; 424/78.31; 424/78.08; 526/328.5; 526/304; 526/306; 526/318; 526/320; 526/321; 526/326; 526/328; 560/41; 560/76; 562/433; 562/496; 564/155; 564/159
[58] Field of Search .................. 526/318, 328.5, 526/304, 306, 320, 321, 326, 328; 424/78.31, 78.35

[56] References Cited

U.S. PATENT DOCUMENTS

| | | | |
|---|---|---|---|
| 4,112,212 | 9/1978 | Choe | 526/318 |
| 4,500,601 | 2/1985 | Whitcomb | 428/403 |
| 5,026,860 | 6/1991 | Buchan et al. | 549/271 |
| 5,385,997 | 1/1995 | Buchan et al. | 526/259 |
| 5,422,395 | 6/1995 | Ooura et al. | 525/60 |

FOREIGN PATENT DOCUMENTS

| | | |
|---|---|---|
| 3-240762 | 10/1991 | Japan . |
| 4-4902 | 1/1992 | Japan . |
| 4-226945 | 8/1992 | Japan . |
| 4-323282 | 11/1992 | Japan . |
| 4-323283 | 11/1992 | Japan . |
| 5-28150 | 4/1993 | Japan . |
| 6-239753 | 8/1994 | Japan . |

OTHER PUBLICATIONS

Chemical Abstracts—"Synthetic High Polymers"—vol. 86, No. 8, Feb. 21, 1977.
Chemical Abstract—"Chemistry of Synthetic High Polymers" vol. 115, No. 10, Sep. 9, 1991.
"Synthesis and Microstructure of Polymers from o-Methacryloyloxybenzoic Acids"—J. San Román et al., Journal of Polymer Science, Part A, Polymer Chemistry, vol. 25, pp. 203–214 (1987).
J. San Román et al. "Application of new coatings for vascular grafts based on polyacrylic systems with antiaggregating activity"—Biomaterials—vol. 15, No. 10, pp. 759–765—1994.

Primary Examiner—Peter F. Kulkosky
Attorney, Agent, or Firm—Armstrong, Westerman, Hattori, McLeland & Naughton

[57] ABSTRACT

Novel acetylsalicylic acid derivatives having general formula (I) are provided, in which $R^1$ is hydrogen or methyl; $R^2$ is —O— or —NH—; and W is hydroxy, halogen, lower alkoxy, lower alkenyloxy, lower alkynyloxy, cycloalkyloxy, aryloxy, aralkyloxy, acyloxy, or —N($R^3$)($R^4$) wherein the lower alkoxy, the lower alkenyloxy, the lower alkynyloxy, the cycloalkyloxy, the aryloxy, the aralkyloxy, and the acyloxy are optionally substituted with hydroxy, carboxyl, lower alkoxy, lower alkyl, halogen, nitro, and amino. The invention also pertains to a polymer made from such derivatives and a medical equipment containing the polymer. The polymer is useful in the prevention of platelet aggregation thereon.

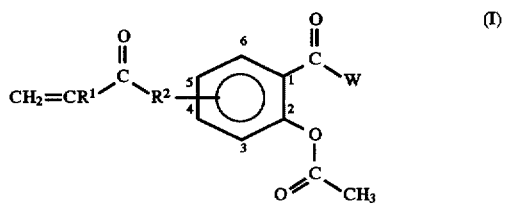

(I)

19 Claims, 2 Drawing Sheets

(METH)ACRYLOYLOXY SUBSTITUTED ACETYLSALICYLATES AND POLYMERS THEREOF

BACKGROUND OF THE INVENTION

1. Field of the Invention

The present invention relates to acrylic or methacrylic derivatives of acetylsalicylic acid, which may be used as a monomer, and a polymer material comprised of the monomer. The polymer material is biocompatible and has antithrombogenicity.

2. Description of Related Art

Polymer materials have been used in medical science. Numerous medical equipment, for example, a catheter, a hose, a container, a membrane etc. are made of polymer materials. The membrane may be used in separating some component in blood, such as in dialysis.

In the medical equipment that is exposed to blood, there has been problem that blood coagulates upon contact with a surface of the medical equipment. The medical equipment may be made of a biocompatible material that does not induce blood coagulation. Alternatively, a surface of the medical equipment is coated by the biocompatible material.

In general, biocompatible polymers contain a hydrophilic group, such as hydroxy group, carboxylic group, carboxylate ion, and amino group for reducing an energy at interface with body fluid such as blood. The biocompatible polymers contain both thy hydrophilic group and lipophilic group so as to form microscopic domain structure for preventing a protein from adhering thereon and platelet aggregation thereon.

Japanese patent publications No. 4-4902 and No. 5-28150- disclose polymer materials including biomaterial originated from living tissues, such as heparin for preventing platelet aggregation. However, the polymer material easily denaturalize, and it requires cost and labor in manufacturing and processing the polymer material. Moreover, the polymer material requires high level of quality control.

J. San Roman has proposed to fix salicylic acid derivatives to a polymer chain so as to improve biocompatibility (Journal of Polymer Science: Part A: Polymer chemistry, Vol. 25, 203–214 (1987) and Biomaterial, Vol. 15, No. 10, 759–765 (1994)). The hydroxy group in the second position in salicylic acid forms ester bonding with the carboxylic group of acrylic acid or methacrylic acid so as to give a monomer and a polymer thereof.

However, radicals, such as superoxide, are present in a human body, and the radicals may sever the ester bonding in the salicylic acid derivatives with the vinyl group, thereby releasing salicylic acid into a human body. Moreover, the position of the particular ester bonding is proposed to be prone to undergo hydrolysis by enzyme activity. Furthermore, the hydroxy group of salicylic acid forming the ester bond plays important roles for the activity of the salicylic acid, and the formation of the ester bond sterically hinders the activity of the salicylic acid while fixed in the polymer chain.

It has been proposed to fix salicylic acid derivatives to a polymer chain by introducing another bond such as ester bond and amide bond in the salicylic acid moiety (Japanese patent applications laid-open No. 3-240762 and No. 4-323283). Japanese patent application laid-open No. 3-240762 discloses 5-methacrylamidosalicylic acid and 5-acrylamidosalicylic acid serving as a monomer. The polymer comprised of the monomer slowly releases 5-aminosalicylic acid working as an anti-inflammation agent and an analgesic. Japanese patent application laid-open No. 4-323283 discloses salicylic (meth)acrylate. However, the disclosure of Japanese patent application laid-open No. 4-323283 is limited to the application to the adhesive.

However, (meth)acrylamidosalicylic acid derivatives have limited antithrombogenicity, and there remains more room for prevent blood coagulation.

SUMMARY OF THE INVENTION

An object of the present invention is to prevent blood coagulation on a surface of a polymer material and to provide a vinyl monomer for the polymer material.

According to the present invention, there is provided an acetylsalicylic acid derivative or a salt thereof having the formula:

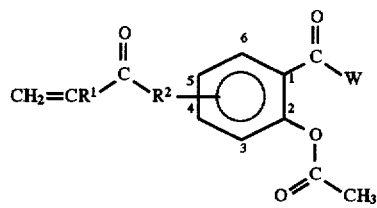

wherein $R^1$ is selected from the group consisting of hydrogen and methyl;

$R^2$ is selected from the group consisting of —O— and —NH—; and

W is selected from the group consisting of hydroxy, halogen, lower alkoxy of 1 to 10 carbon atoms, lower alkenyloxy of 2 to 10 carbon atoms, lower alkynyloxy of 2 to 10 carbon atoms, cycloalkyloxy of 3 to 10 carbon atoms, aryloxy, aralkyloxy, acyloxy, and —N($R^3$)($R^4$) wherein $R^3$ and $R^4$ are independently selected from the group consisting of hydrogen, lower alkyl, cycloalkyl, aryl, hydroxy and alkoxy, wherein said lower alkoxy, said lower alkenyloxy, said lower alkynyloxy, said cycloalkyloxy, said aryloxy, said aralkyloxy, said acyloxy are optionally substituted with hydroxy, carboxyl, lower alkoxy, lower alkyl, halogen, nitro, and amino.

W is preferably hydroxy, lower alkoxy of 1 to 6 carbon atoms, aryloxy, and —N($R^3$)($R^4$) wherein $R^3$ and $R^4$ are independently selected from the group consisting of hydrogen and lower alkyl. W is further preferably hydroxy, lower alkoxy of 1 to 4 carbon atoms, phenoxy, and amino (—$NH_2$), and most preferably hydroxy.

$R^2$ is preferably —NH—.

According to the present invention, there is provided a novel polymer material comprising an acetylsalicylic acid derivative or a salt thereof having the formula:

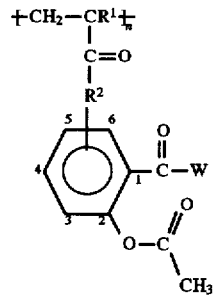

wherein $R^1$ is selected from the group consisting of hydrogen and methyl;

$R^2$ is selected from the group consisting of —O— and —NH—; and

W is selected from the group consisting of hydroxy, lower alkoxy of 1 to 10 carbon atoms, lower alkenyloxy of 2 to 10 carbon atoms, lower alkynyloxy of 2 to 10 carbon atoms, cycloalkyloxy of 3 to 10 carbon atoms, aryloxy, aralkyloxy, acyloxy, and —N($R^3$)($R^4$) wherein $R^3$ and $R^4$ are independently selected from the group consisting of hydrogen, lower alkyl, cycloalkyl, aryl, hydroxy and alkoxy, wherein said lower alkoxy, said lower alkenyloxy, said lower alkynyloxy, said cycloalkyloxy, said aryloxy, and said aralkyloxy, said acyloxy are optionally substituted with hydroxy, carboxyl, lower alkoxy, lower alkyl, halogen, nitro, and amino; and n is an integer.

Preferably, a polymer material further comprises a monomeric unit having the formula:

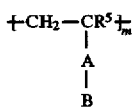

wherein $R^5$ is selected from the group consisting of hydrogen, methyl, and halogen;

A is selected from the group consisting of direct bonding, oxygen, —C(=O)—O—, —O—C(=O)—, —N($R^6$)—C(=O)—, —C(=O)—N($R^6$)—, and alkylene of 1 to 3 carbon atoms wherein $R^6$ is selected from the group consisting of hydrogen and lower alkyl wherein the lower alkyl is optionally substituted with amino or alkylamino;

B is selected from the group consisting of hydrogen, halogen, alkyl, alkenyl, alkynyl, cycloalkyl of 3 to 10 carbon atoms, aryl of 3 to 16 carbon atoms, 4 to 8 member heterocyclic ring containing 1, 2 or 3 heteroatoms wherein said heteroatoms are at least one of N and O, and aralkyl, wherein said alkyl, said alkenyl, said alkynyl, said cycloalkyl, said aryl, said heterocyclic ting and said aralkyl are optionally substituted with hydroxy, carboxyl, lower alkoxy, lower alkoxycarbonyl, lower alkyl, halogen, nitro, amino, and alkylamino; and m is an integer.

Preferably, $R^5$ is selected from the group consisting of hydrogen, methyl, and chlorine; A is selected from the group consisting of —C(=O)—O— and —C(=O)—NH—; and B is selected from the group consisting of hydrogen, alkyl of 1 to 20 carbon atoms, alkenyl of 1 to 20 carbon atoms, alkynyl of 1 to 20 carbons, cycloalkyl of 3 to 8 carbon atoms, aryl of 5 to 12 carbon atoms, and 5 to 7 member heterocyclic ring containing 1 or 2 heteroatoms.

According to the present invention, there is provided a medical equipment comprising the polymer material.

DETAILED DESCRIPTION OF THE PREFERRED EMBODIMENTS

Figure 1:
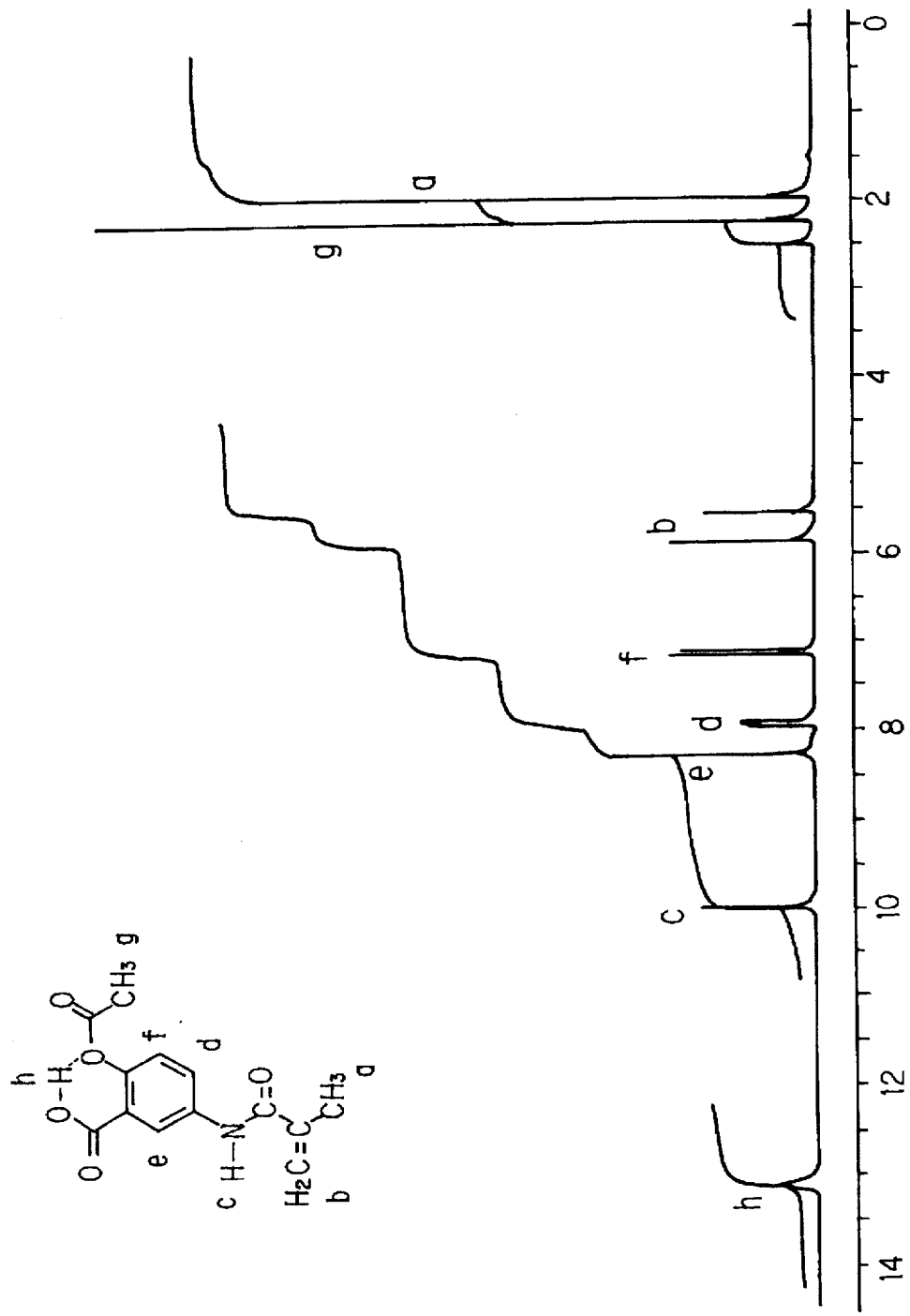
FIG. 1 is a $^1$H-NMR spectrum of 2-acetyl-5-methacrylamidosalicylic acid obtained in Example 3.

A preferred embodiment of the present invention is a compound of the formula I:

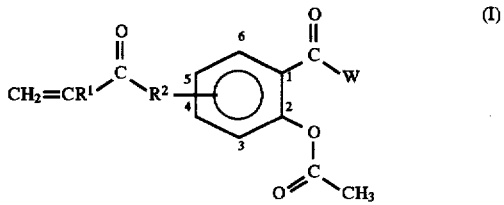

wherein $R^1$ is selected from the group consisting of hydrogen and methyl;

$R^2$ is selected from the group consisting of —O— and —NH—; and

W is selected from the group consisting of hydroxy, halogen, lower alkoxy of 1 to 10 carbon atoms, lower alkenyloxy of 2 to 10 carbon atoms, lower alkynyloxy of 2 to 10 carbon atoms, cycloalkyloxy of 3 to 10 carbon atoms, aryloxy, aralkyloxy, acyloxy, and —N($R^3$)($R^4$) wherein $R^3$ and $R^4$ are independently selected from the group consisting of hydrogen, lower alkyl, cycloalkyl, aryl, hydroxy and alkoxy, wherein said lower alkoxy, said lower alkenyloxy, said lower alkynyloxy, said cycloalkyloxy, said aryloxy, said aralkyloxy, said acyloxy are optionally substituted with hydroxy, carboxyl, lower alkoxy, lower alkyl, halogen, nitro, and amino.

A compound (I) includes an amido derivative (Ia) and an ester derivative (Ib), which further includes derivatives (Ic) and (Id) where W is hydroxy. The amido derivative (Ia) is expected to be less prone to undergo hydrolysis, and in some application therefore preferable.

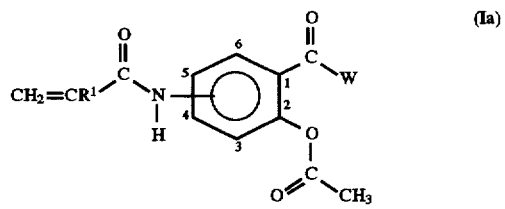

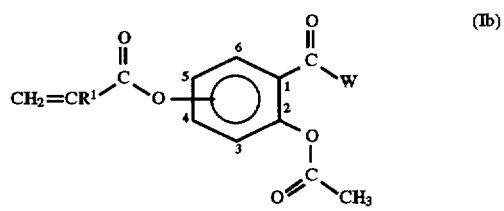

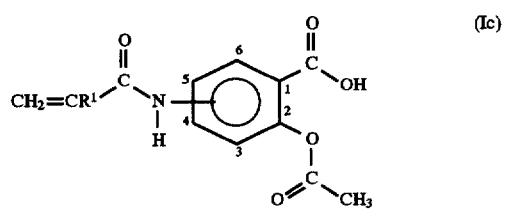

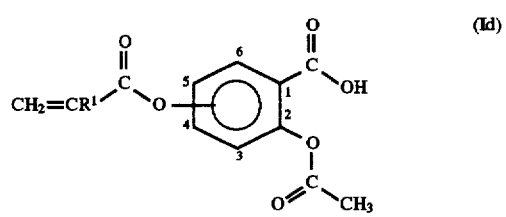

As utilized herein, the term "(meth)acrylic" refers to acrylic or methacrylic. Similarly, the term "(meth)acrylate" refers to acrylate or methacrylate.

The term "lower alkyl", alone or in combination, means alkyl containing from 1 to 10, preferably from 1 to 8 carbon atoms and more preferably from 1 to 6 carbon atoms. Examples of such "lower alkyl" includes methyl, ethyl, n-propyl, isopropyl, n-butyl, isobutyl, sec-butyl, tert-butyl, pentyl, iso-amyl, hexyl and the like. "Alkyl" preferably contains from 1 to 40 carbon atoms, and further preferably contains from 1 to 20 carbon atoms, and most preferably lower alkyl.

The term "lower alkenyl" refers to an unsaturated acyclic hydrocarbon is so much as it contains at least one double bond. The lower alkenyl contains from 2 to 10 carbon atoms, preferably from 2 to 8 carbon atoms and more preferably 2 to 6 carbon atoms. Examples of lower alkenyl include ethenyl, propenyl, 1-methylvinyl, butenyl, 2-methylbuten-1-yl, penten-1-yl, 3-methylbuten-1-yl, hexen-1-yl, 2-2-methylbuten-1-yl, and octen-1-yl and the like. "Alkenyl" preferably contains from 1 to 40 carbon atoms, and further preferably contains from 1 to 20 carbon atoms, and most preferably lower alkenyl.

The term "lower alkynyl" refers to an unsaturated acyclic hydrocarbon in so much as it contains one or more triple bonds. The "lower alkenyl" contains from 2 to 10 carbon atoms, preferably from 2 to 8 carbon atoms and more preferably 2 to 6 carbon atoms. Examples of lower alkynyl include ethynyl, propynyl, 1-methylethynyl, butynyl, 2-methylbutyn-1-yl, pentyn-1-yl, 3-methylbutyn-1-yl, hexyn-1-yl, 2-2-methylbutyn-1-yl, and octyn-1-yl and the like. "Alkynyl" preferably contains from 1 to 40 carbon atoms, and further preferably contains from 1 to 20 carbon atoms, and most preferably lower alkynyl.

The term "cycloalkyl" refers to an aliphatic radical in a ring with 3 to 10 carbon atoms, and preferably from 3 to about 8 carbon atoms. Examples of suitable cycloalkyl include cyclopropyl, cyclopropylenyl, cyclobutyl, cyclopentyl, cyclohexyl, 2-cyclohexen-1-ylenyl, and cyclohexenyl and the like.

The term "aryl" contains from 3 to 16 carbon atoms, preferably from 5 to 12 carbon atoms, more preferably from 6 to 10 carbon atoms. Examples of suitable aryl includes phenyl, naphthyl, indacenyl, and anthracenyl, and the like.

"Heterocyclic ring" may be saturated or unsaturated. Examples of saturated heterocycle ring containing N include pyrrole, imidazole, pyrazole, pyridine, indole, benzimidazole, and quinoline, and the like. Heterocycle ring containing N further includes pyrrolidine, imidazolidine piperidine, piperzaine, indoline, and the like. Examples of saturated heterocyclic ring containing O include furan, and benzofuran, and the like. Heterocyclic ring containing O further includes tetrahydrofuran, and chroman, and the like. Examples of saturated heterocyclic ring containing N and O include oxazole, furazan, and benzoxazole, and the like. Examples of heterocyclic ring containing N and O further includes dihydrooxazole, morpholine, and the like.

The term "lower alkoxy", alone or in combination, means an alkyl ether radical wherein the term alkyl is as defined above. The "lower alkoxy" preferably contains from 1 to 10, preferably from 1 to 8 carbon atoms and more preferably from 1 to 6 carbon atoms. Examples of suitable "lower alkoxy" include methoxy, ethoxy, n-propoxy, isopropoxy, n-butoxy, iso-butoxy, sec-butoxy, and tert-butoxy and the like.

The term "alkenyloxy" means an alkenyl ether radical wherein the term alkenyl is as defined above. The "lower alkenyloxy" preferably contains from 1 to 10, preferably from 1 to 8 carbon atoms and more preferably from 1 to 6 carbon atoms. Examples of alkenyloxy include ethenyloxy, propenyloxy, 1-methylvinyloxy, butenyloxy, 2-methylbuten-1-yloxy, penten-1-yloxy, 3-methylbuten-1-yloxy, hexen-1-yloxy, 2-2-methylbuten-1-yloxy, and octen-1-yloxy and the like.

The term "alkynyloxy" means an alkynyl ether radical wherein the term alkynyl is as defined above. The "lower alkynyloxy" preferably contains 1 to 10, preferably from 1 to 8 carbon atoms and more preferably from 1 to 6 carbon atoms. Examples of alkynyloxy include ethynyloxy, propynyloxy, 1-methylethynyloxy, butynyloxy, 2-methylbutyn-1-yloxy, pentyn-1-yloxy, 3-methylbutyn-1-yloxy, hexyn-1-yloxy, 2-2-methylbutyn-1-yloxy, and octyn-1-yloxy, and the like.

The term "cycloalkyloxy" means a cycloalkyl ether radical wherein the term cycloalkyl is as defined above. Examples include cyclopropyloxy, cyclopropylenyloxy, cyclobutyloxy, cyclopentyloxy, cyclohexyloxy, 2-cyclohexen-1-ylenyloxy, and cyclohexenyloxy, and the like.

The term "aryloxy" means an aryl ether radical wherein the term aryl is as defined above. Suitable examples include phenoxy, tolyloxy, xylyloxy, and naphthyloxy, and the like.

Examples of "aralkyl" include benzyl, phenethyl, styryl, cinnamyl, and the like. Examples of "aralkyloxy" include benzyloxy, phenethyloxy, styryloxy, cinnamyloxy, and the like.

The term "acyloxy" includes alkanoyloxy, cycloalkylcarbonyloxy, arylcarbonyloxy, aralkylcarbonyloxy and the like. Examples of alkanoyloxy include formyloxy, acetoxy, ethylcarbonyloxy, propylcarbonyloxy, and butylcarbonyloxy, and the like. Examples of cycloalkylcarbonyloxy include cyclobutylcarbonyloxy, cyclopentylcarbonyloxy, cyclohexylcarbonyloxy, 2-cyclohexen-1-ylenylcarbonyloxy, and cyclohexenyl and the like. Examples of arylcarbonyloxy include benzoyloxy, benzenedicarbonyloxy, and naphthalenecarbonyloxy, and the like. Examples of aralkylcarbonyloxy includes phenylmethylcarbonyloxy, and the like.

The term "halogen" includes fluorine, chlorine, bromine, and iodine. When halogen substitutes hydrogen in an alkyl moiety, fluorine, chlorine, and bromine are preferable. When halogen substitutes hydrogen in aryl moiety, chlorine and bromine are preferable.

The term "alkylamino" means an alkyl amine radical wherein the term alkyl is as defined above. Examples of alkylamino include N-methylamino, N,N-dimethylamino, N-ethylamino, and N-methyl-N-ethylamino, and the like.

The term "carboxylic acid derivative" includes the following:

1. ester (COOR)
   wherein R can be lower alkyl, cycloalkyl or aryl
2. amide (CONR'R")
   wherein R' and R" are independently selected from the group consisting of hydrogen, alkyl, cycloalkyl, aryl, hydroxy or alkoxy
3. acid anhydride (CO—O—CO—R'")
   wherein R'" can be lower alkyl, cycloalkyl or aryl.

The term "salt" refers to a salt prepared by contacting a compound of formula (I) with a base. Examples of salts include metallic salts made from alkali metal such as Na and K, alkaline earth metal such as Ca and Mg, aluminum, and zinc or organic salts made from tetraalkylamine, N,N-dibenzylethylenediamine. All of these salts may be prepared by conventional means by reacting, for example, the appropriate base with the corresponding compound of formula (I).

In the structures and formula herein, the bond drawn across a bond of an aromatic ring can be to any available atom on the aromatic ring.

The compounds in this invention can exist in various isomeric forms and all such isomeric forms are meant to be included. Tautomeric forms are also included in the invention.

The compounds listed above may be prepared by standard synthetic methods. Two general synthetic sequences are outlined in Schemes 1 and 2.

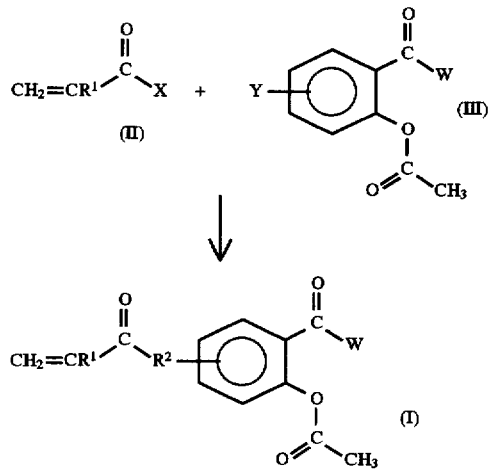

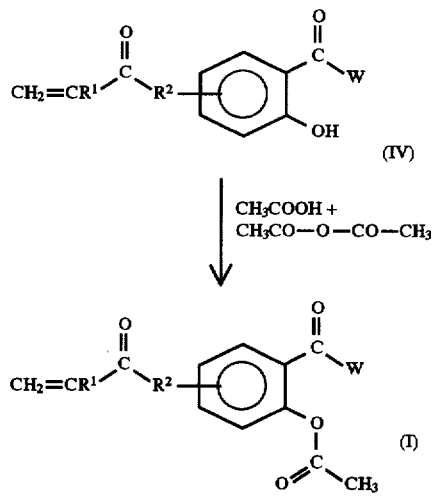

($R^1$, $R^2$, and W have the aforementioned meaning. X refers to a favorable leaving group, including halogen such as chlorine and bromine, alkoxy, aryloxy, and acyloxy. Y refers hydroxy (—OH) or amine (—$NH_2$).)

In Scheme 1, (meth)acrylic derivative (II) is reacted with acetylsalicylic acid derivative (III) to give acetylsalicylic acid derivative (I). The (meth)acrylic derivative (II) may be alkyl(meth)acrylate, (meth)acrylic anhydride, and (meth) acrylate halide.

The reaction may be carried out in an organic solvent, such as acetonitrile, tetrahydrofuran, methylene chloride, chloroform, tetrachloromethane, dichloroethane, N,N-dimethylformamide, dimethyl sulfoxide, and the like. The organic solvent is preferably free of water. Preferably an inhibitor for prevent polymerization is present in the solvent. The inhibitor includes hydroquinone, dimethyl 1,4-cyclohexanedicarboxylate, and tert-butyl hydroxytoluene.

The reaction may be carried out at temperatures ranging from −77° C. to room temperature, at room temperature, or temperatures ranging from room temperature to 150° C. Temperatures ranging from 40° C. to 150° C. is preferable to facilitate the reaction. The reaction is preferably carried out in an inert atmosphere, such as in nitrogen or in argon.

In Scheme 2, salicylic acid derivative (IV) is acetylated to give acetylsalicylic acid derivative (I). Typically, a mixture of acetic acid and acetic anhydride serves as an acetylating agent and a solvent. Alternatively, either acetic acid or acetic anhydride may be used.

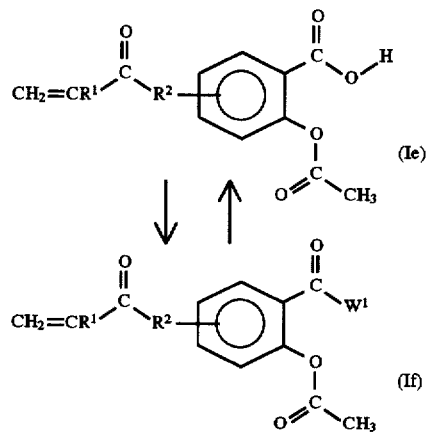

($R^1$, $R^2$, and W have the aforementioned meaning. $W^1$ is the same as W except that $W^1$ excludes hydroxy.)

In Scheme 3, a compound of formula (Ie) may be converted to another compound of formula (If) and vice versa. A vinyl derivative of acetylsalicylic acid (Ie) may be reacted with a compound $W^1$—Z to give another acetylsalicylic acid derivative (If), wherein Z is a leaving group.

Alternatively, acetylsalicylic acid derivative (If) may be hydrolyzed to give acetylsalicylic acid (Ie). The hydrolysis reaction may be carried out in acidic or alkaline conditions.

In the transformation reactions in Scheme 3, preferably an inhibitor for preventing polymerization is present. The inhibitor includes hydroquinone, dimethyl 1,4-cyclohexanedicarboxylate, and tert-butyl hydroxytoluene.

The reaction is preferably carried out in acidic conditions. For example, a strong acid is added as a catalyst. The acid may be inorganic, such as hydrochloric acid, sulfuric acid, phosphoric acid and the like. The organic acid may be used also.

For example, to prepare alkyl ester, to a solution of a monomer in alcohol was added 1 to 2% by weight of a polymerization inhibitor and 0.1 to 1% of sulfuric acid, and the solution is subject to reflux for several hours. After evaporating the solvent, the remaining residue is recrystallized by a mixture of water and the alcohol.

The compound thus obtained is favorably purified, for example, by chromatography and recrystallization. The purification is especially required in the application to make a polymer.

The compound of formula (I) may be polymerized by a conventional free radical polymerization in the presence of an initiator, for example, 2,2'-azobisisobutyronitrile, benzoyl peroxide, and the like.

Alternatively, the compound (I) may undergo anionic polymerization in the presence of strong base, for example, alkali metal such as lithium and sodium and organometallic compound such as aluminum lithium hydride.

The acetylsalicylic acid derivative of the present invention may be copolymerized with another monomer. The resulting copolymer may be random copolymer, alternating copolymer, block copolymer and graft copolymer.

The favorable monomer for the copolymerization includes $CH_2=C(R^5)$-A-B wherein $R^5$, A, and B have the aforementioned meaning. Examples of the group -A-B is listed as follows:

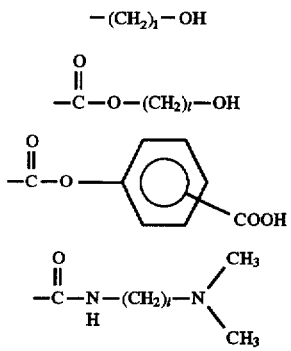

(l is an integer of 1 to 40, preferably 1 to 30, and further preferably 1 to 20.)

The monomer may be a vinyl monomer including a (meth)acrylic acid derivative. The (meth)acrylic acid derivative includes (meth)acrylic acid, metallic salts of (meth) acrylate such as sodium (meth)acrylate and potassium (meth)acrylate; alkyl (meth)acrylate such as methyl (meth) acrylate, octyl (meth)acrylate, tridecyl (meth)acrylate, and octadecyl (meth)acrylate; aralkyl (meth)acrylate such as benzyl (meth)acrylate; aryl (meth)acrylate, such as phenyl (meth)acrylate; and (meth)acrylonitrile. The (meth)acrylic acid derivative further includes substituted alkyl (meth) acrylate, such as alkoxyalkyl (meth)acrylate, for example, 2-methoxyethyl (meth)acrylate, 3,6-dioxaoctane-8-ol-1-yl (meth)acrylate; hydroxyalkyl (meth)acrylate, for example, 2-hydroxyethyl (meth)acrylate; halogenated alkyl (meth) acrylate, for example, 2,2,2-trifluoroethyl (meth)acrylate; alkylaminoalkyl (meth)acrylate, for example, 2-(dimethylamino)ethyl (meth)acrylate; and glycidyl (meth) acrylate. The (meth)acrylic acid derivative further includes (meth)acrylamide derivative, for example, (meth) acrylamide, N-methyl(meth)acrylamide, N,N-dimethyl (meth)acrylamide, N-[3-(N,N-dimethylamino)propyl] (meth)acrylamide. The (meth)acrylic acid derivative may contain a heterocyclic ring, and examples of such derivative include tetrahydrofurfuryl (meth)acrylate and (meth) acryloylmolpholine.

Alternatively, the vinyl monomer includes: α-olefine such as ethylene, propylene, and 2-methyl-1-propene; acyloxyvinyl such as vinyl acetate, vinyl propionate, vinyl butyrate, vinyl pivarate, and vinyl benzoate; vinyl ether such as vinyl ethyl ether, and vinyl butyl ether; vinyl chloride; and N-vinylpyrrolidone.

The monomer is not limited to the vinyl monomer. The monomer may be vinylidene chloride and maleic anhydride.

The medical equipment includes a catheter, a hose, a container and an artificial organ such as heart. The medical equipment may be made of the polymer material of the present invention. Alternatively, a surface of the medical equipment is coated by the polymer material.

The polymer material of the present invention contains acetylsalicylic acid derivatives so as to prevent platelet aggregation thereon. Moreover, in the polymer material of the present invention, acetylsalicylic acid derivatives are fixed to a polymer chain by means of the ester bond or amide bond in the acetylsalicylic acid moiety that 2-acetyl moiety and the carboxylic moiety in the acetylsalicylic acid moiety remain intact, thereby the acetylsalicylic acid moiety is expected to function as an aspirin while fixed thereto. Therefore, the polymer material is expected to work as an antibacterial agent.

Furthermore, in the polymer material of the present invention, acetylsalicylic acid derivatives, that is aminoacetylsalicylic acid or hydroxyacetylsalicylic acid, are slowly released to fluid in contact with the polymer material so as to prevent intimation and to relieve pain and fever.

EXAMPLES

EXAMPLE 1

Synthesis of 2-acetyl-4-methacryloyloxysalicylic acid (1) 2-acetyl-4-hydroxysalicylic acid (intermediate)

2,4-dihydroxybenzoic acid (32.4 millimole, 5.0 g) was suspended in a mixture of acetic anhydride (4.0 g) and acetic acid (5.0 g). After sealing the suspension, its temperatures was raised to 60° C., and the suspension was kept at 60° C. for 30 min while stirring. Then, a mixture (1.0 g) of concentrated sulfuric acid (1 part) with hydrochloric acid (10 parts) was added to the suspension, followed by raising its temperature to 90° C., and kept at 90° C. for one hour to proceed the reaction.

After the reaction was over, the suspension was cooled to 0° C. so as to precipitate colorless powder. The precipitate was filtrated, washed by dichloromethane, and recrystallized by warm water at 50° C.

After filtration, the powder was dried under a reduced pressure to give colorless powder of 2-acetyl-4-hydroxysalicylic acid: yield 3.82 g, 60.1%.

(2) 2-acetyl-4-methacryloyloxysalicylic acid (the present invention)

2-acetyl-4-hydroxysalicylic acid (15.0 millimole, 2.9 g) and butylhydroxytoluene (10 mg) was dissolved in tetrahydrofuran (THF). To the solution was added triethylamine (0.5 g), and the solution was cooled to 0° C. by ice bath. While stirring under a flow of nitrogen gas, methacryl chloride (20 millimole, 2.41 g) was added to the solution using a syringe over a period of 20 minutes, and the solution was kept stirred for another hour after completing the addition. After the reaction was over, the solvent was evaporated to give pale yellow powder. The powder was washed by dichloromethane and recrystallized by an aqueous solution of 0.5% hydroquinone. Dried under a reduced pressure, colorless crystal having a needle shape was obtained: m.p. 152.7° C.; yield 2.54 g, 64.1%.

| Elemental analysis (calculated as $C_{13}H_{12}O_6$) | | |
|---|---|---|
| | C | H |
| calc. (%) | 59.09 | 4.58 |
| exp. (%) | 59.03 | 4.62 |

¹H-NMR(DMSO-d₆, ppm)
δ: 13.08 (COO<u>H</u>, 8.00, 7.96, 7.21, 7.20, 7.16, 7.15, 7.10, 7.09 (C₆<u>H</u>₃, 5.87, 5.62 (=C<u>H</u>₂), 2.25 (OCOC<u>H</u>₃), 1.99 (C<u>H</u>₃).

EXAMPLE 2

Synthesis of 2-acetyl-5-methacryloyloxysalicylic acid (1) 2-acetyl-5-hydroxysalicylic acid (intermediate)

2,5-dihydroxybenzoic acid was used as a starting material. The same procedures as the step (1) in Example 1 gave 2-acetyl-5-hydroxysalicylic acid as colorless powder: yield 4.33 g, 68.1%.

(2) 2-acetyl-5-methacryloyloxysalicylic acid (the present invention)

2-acetyl-5-hydroxysalicylic acid was used as a starting material. The same procedures as the step (2) in Example 1 gave 2-acetyl-5-methacryloyloxysalicylic acid as colorless crystal: mp. 149.6° C.; yield 3.27 g, 82.5%

| Elemental analysis (calculated as $C_{13}H_{12}O_6$) | | |
|---|---|---|
|  | C | H |
| calc. (%) | 59.09 | 4.58 |
| exp. (%) | 59.11 | 4.54 |

$^1$H-NMR(DMSO-d$_6$, ppm)
δ: 12.74 (COO$\underline{H}$), 7.96, 7.30, 7.27 (C$_6\underline{H}_3$), 6.21, 5.89 (=C$\underline{H}_2$), 2.19 (OCOC$\underline{H}_3$), 1.97 (C$\underline{H}_3$).

EXAMPLE 3

Synthesis of 2-acetyl-5-methacrylamidosalicylic acid (1) 5-methacrylamidosalicylic acid (intermediate)

5-aminosalicylic acid (50.0 millimole, 7.7 g), methacrylic anhydride (60.0 millimole, 9.3 g), and butylhydroxytoluene (20.0 mg) were suspended in dimethyl sulfoxide (50.0 ml). After sealing the suspension, its temperature was raised to 60° C. by oil bath while stirring, and the suspension became homogeneous quickly. The mixture was further kept at 60° C. for five hours while stirring to give a viscous liquid having dark brown color. The reaction was kept proceeding till the viscous liquid gave brown precipitate. The precipitate was filtrated, washed by dichloromethane to give brownish gray powder. The powder was recrystallized by a solution of 0.5% hydroquinone in methanol, and dried under a reduced pressure to give brownish gray crystal of 5-methacrylamidosalicylic acid: yield 9.27 g, 83.8%.

(2) 2-acetyl-5-methacrylamidosalicylic acid (the present invention)

5-methacrylamidosalicylic acid (30 millimole, 6.7 g) was mixed with butylhydroxytoluene (20 mg), acetic anhydride (10.0 g), and acetic acid (15.0 g). After sealing the solution, its temperatures was raised to 60° C., and the solution was kept at 60° C. for 30 min while stirring. Then, a mixture (1.0 g) of concentrated sulfuric acid (1 part) with hydrochloric acid (10 parts) was added to the solution, followed by raising its temperature to 90° C., and kept at 90° C. for one hour to proceed the reaction. After the reaction was over, the solution was stood to cool to room temperature to give brown crystal. The crystal was filtrated, and recrystallized by a solution of 0.5% hydroquinone in methanol. Dried under a reduced pressure, 2-acetyl-5-methacrylamidosalicylic acid was obtained as pale reddish brown crystal having a needle shape: mp. 192.4° C., yield 2.54 g, 64.1%.

| Elemental analysis (calculated as $C_{13}H_{13}O_5N$) | | | |
|---|---|---|---|
|  | C | H | N |
| calc. (%) | 59.31 | 4.98 | 5.32 |
| exp. (%) | 59.31 | 4.98 | 5.17 |

$^1$H-NMR(DMSO-d$_6$, ppm)
δ: 13.11 (COO$\underline{H}$), 9.99 (CON$\underline{H}$), 8.27, 7.96, 7.93, 7.92, 7.16, 7.12 (C$_6\underline{H}_3$), 5.85, 5.55 (=C$\underline{H}_2$, 2.23 (OCOC$\underline{H}_3$), 1.96 (C$\underline{H}_3$).

EXAMPLE 4

Synthesis of 2-acetyl-4-methacrylamidosalicylic acid (1) 4-methacrylamidosalicylic acid (intermediate)

4-aminosalicylic acid was used as a starting material. The same procedures as the step (1) in Example 3 gave 4-methacrylamidosalicylic acid as yellow powder: yield 7.64 g, 68.9%.

(2) 2-acetyl-4-methacrylamidosalicylic acid (the present invention)

4-methacrylamidosalicylic acid was used as a starting material. The same procedures as the step (2) in Example 3 gave 2-acetyl-4-methacrylamidosalicylic acid as pale yellow crystal having a needle shape: mp. 178.1° C.; yield 3.51 g, 44.8%.

| Elemental analysis (calculated as $C_{13}H_{13}O_5N$) | | | |
|---|---|---|---|
|  | C | H | N |
| calc. (%) | 59.31 | 4.98 | 5.32 |
| exp. (%) | 59.28 | 5.00 | 5.38 |

$^1$H-NMR(DMSO-d$_6$, ppm)
δ: 12.86 (COO$\underline{H}$), 10.18 (CON$\underline{H}$), 7.93, 7.92, 7.88, 7.74, 7.65, 7.61 (C$_6\underline{H}_3$), 5.85, 5.60 (=C$\underline{H}_2$), 2.25 (OCOC$\underline{H}_3$), 1.95 (C$\underline{H}_3$).

Figure 2:
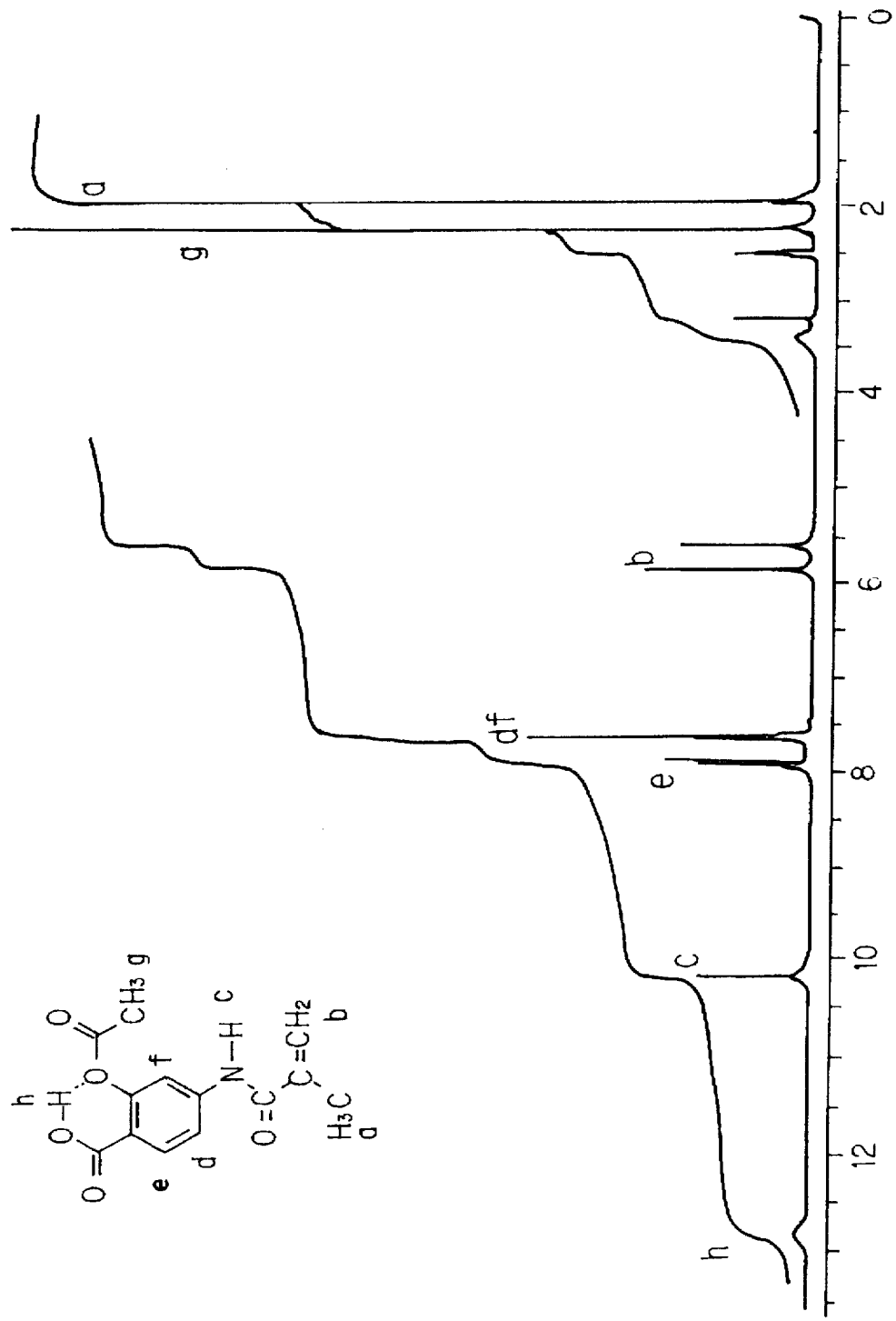
FIG. 2 is a $^1$H-NMR spectrum of 2-acetyl-4-methacrylamidosalicylic acid obtained in Example 4.

A $^1$H-NMR spectrum of the compound is shown in FIG. 2.

EXAMPLE 5

Synthesis of 2-acetyl-4-acrylamidosalicylic acid (1) 4-acrylamidosalicylic acid (intermediate)

Acrylic anhydride was used as a starting material. The same procedures as the step (1) in Example 4 gave 4-acrylamidosalicylic acid as yellow powder: yield 8.22 g, 79.3%.

(2) 2-acetyl-4-acrylamidosalicylic acid (the present invention)

4-acrylamidosalicylic acid was used as a starting material. The same procedures as the step (2) in Example 4 gave 2-acetyl-4-acrylamidosalicylic acid as yellowish white crystal having a needle shape: mp. 171.2° C.; yield 3.51 g, 44.8%.

| Elemental analysis (calculated as $C_{12}H_{11}O_5N$) | | | |
|---|---|---|---|
|  | C | H | N |
| calc. (%) | 57.83 | 4.45 | 5.62 |
| exp. (%) | 58.08 | 4.63 | 5.68 |

$^1$H-NMR(DMSO-d$_6$, ppm)
δ: 12.81 (COO$\underline{H}$), 10.56 (CON$\underline{H}$), 7.90, 7.65, 7.54, 7.53 (C$_6\underline{H}_3$), 6.44, 6.39, 5.86, 5.85, 5.81, 5.80 (=C$\underline{H}_2$), 6.35, 6.34 (C$\underline{H}$), 2.25 (OCOC$\underline{H}_3$).

EXAMPLE 6

Synthesis of 2-acetyl-4-methacryloyloxysalicylic acid (1) 4-methacryloyloxysalicylic acid (intermediate)

2,4-dihydroxybenzoic acid (64.88 millimole, 10.0 g) was dissolved in an aqueous solution (300 g) of sodium hydroxide (1.7% by weight) to give an orange solution and the solution was cooled to 0° C. by ice bath. While stirring under a flow of nitrogen gas, a solution of methacryl chloride (8.0 g) in dichoromethane (100 ml) was added to the solution over a period of 60 minutes, and the solution was kept stirred at 0° C. for four hours after completing the addition. After the solution was stood to slowly warm to room temperature, the solution was further stirred overnight. The aqueous layer was separated from the organic layer, and to the aqueous layer was added an aqueous solution of 1N HCl so as to adjust its pH to 1. The solution was stood overnight to give colorless powder, and the powder was filtrated. The powder was washed by cold acidic water (100 ml) three times. After drying the powder under a reduced pressure at room temperature, the powder was recrystallized at 60° C. by an aqueous solution of methanol containing a small amount of hydroquinone to give colorless crystal having a needle shape: yield 10.11 g, 70.1%.

(2) 2-acetyl-4-methacryloyloxysalicylic acid (the present invention)

4-methacryloyloxysalicylic add (45 millimole, 10.0 g) was suspended in a mixture of acetic anhydride (8.0 g) and acetic acid (10.0 g). After sealing the suspension, its temperatures was raised to 60° C., and the suspension was kept at 60° C. for 30 minutes while stirring. Then, a mixture (2.0 g) of concentrated sulfuric acid (1 part) with hydrochloric acid (10 parts) was added to the suspension, followed by raising its temperature to 90° C., and kept at 90° C. for one hour to proceed the reaction.

After the reaction was over, the suspension was cooled to 0° C. so as to precipitate colorless powder, and the powder was filtrated. After drying the powder under a reduced pressure at room temperature, the powder was recrystallized at 60° C. by an aqueous solution of methanol containing a small amount of hydroquinone to give colorless crystal having a needle shape: yield 9.32 g, 78.4%.

Elemental analysis (calculated as $C_{13}H_{12}O_6$)

|  | C | H |
|---|---|---|
| calc. (%) | 59.09 | 4.58 |
| exp. (%) | 59.02 | 4.63 |

$^1$H-NMR(DMSO-$d_6$, ppm)

δ: 13.08 (COOH), 8.00, 7.96, 7.21, 7.20, 7.16, 7.15, 7.10, 7.09 ($C_6\underline{H}_3$), 5.87, 5.62 (=$C\underline{H}_2$), 2.25 (OCOC$\underline{H}_3$), 1.99 (C$\underline{H}_3$).

EXAMPLE 7

Synthesis of sodium 2-acetyl-5-methacrylamidosalicylate 2-acetyl-5-methacrylamidosalicylic acid and hydroquinone (0.5% by weight) were dissolved in an aqueous solution of excess sodium hydrogencarbonate. The solution was stirred at temperatures of 40° C. to 50° C. The solvent was removed under acidic conditions. The remaining powder was recrystallized by a mixture of water and ethanol to give sodium 2-acetyl-5-methacrylamidosalicylate.

EXAMPLE 8

Synthesis of methyl 2-acetyl-5-methacrylamidosalicylate

To a solution of 2-acetyl-5-methacrylamidosalicylic acid and 1% by weight of hydroquinone in methanol was added 0.5% by weight of concentrated sulfuric acid, and the solution was subject to reflux for several hours. After evaporating the solvent, the remaining residue was recrystallized by a mixture of water and methanol to give methyl 2-acetyl-5-methacrylamidosalicylate.

EXAMPLE 9

Synthesis of phenyl 2-acetyl-5-methacrylamidosalicylate 2-acetyl-5-methacrylamidosalicylic acid (1 part by mole), dicyclohexyl carbodiimide (1.1 part by mole), phenol (1.1 part by mole), and dimethylaminopyridine (about 0.1 part by mole) serving as a catalyst are dissolved in dry dichloromethane (50 ml). The solution is stirred at room temperature overnight. After the reaction, the precipitate including dicyclohexyl carbodiimide urea is removed by filtration. The solution is washed by distilled water three times, by an aqueous solution of 5% by weight of acetic acid three times, and further by distilled water three times. The solution is filtrated again to remove the precipitate. The solvent is removed by evaporation, and the residue is recrystallized to give phenyl 2-acetyl-5-methacrylamidosalicylate.

EXAMPLE 10

Synthesis of salicyl 2-acetyl-5-methacrylamidosalicylate

To a solution of 2-acetyl-5-methacrylamidosalicylic acid (1 part by mole), dicyclohexyl carbodiimide (1.1 part by mole) in dry dichloromethane is added N-hydroxysuccinimide. To the solution is further added salicylic acid (1.1 part by mole). The solution is stirred at room temperature overnight. After the reaction, the precipitate including dicyclohexyl carbodiimide urea is removed by filtration. The solution is washed by distilled water three times, by an aqueous solution of 5% by weight of acetic acid three times, and further by distilled water three times. The solution is filtrated again to remove the precipitate. The solvent is removed by evaporation, and the residue is recrystallized to give salicyl 2-acetyl-5-methacrylamidosalicylate.

EXAMPLE 11

Synthesis of 2-acetyl-5-methacrylamidosalicylamide

The same procedures as Example 10 except that an aqueous solution of 30% ammonia is replaced with salicylic acid give 2-acetyl-5-methacrylamidosalicylamide.

EXAMPLES 12–15

Polymers of 2-acetyl-5-methacrylamidosalicylic acid were prepared by the free radical polymerization of a mixture of the corresponding monomers in N,N-dimethylformamide. 2,2'-Azobisisobutyronitrile (AIBN) was used as initiator, and the reaction was carried out for 48 hours in high vacuum at 60° C. In Examples 12–14, 2-acetyl-5-methacrylamidosalicylic acid was polymerized with 2-hydroxyethyl methacrylate to give a random copolymer. In Example 15, 2-acetyl-5-methacrylamidosalicylic acid was polymerized in the same procedures to give a homopolymer. Polymers were isolated by the precipitation of the reaction medium in a mixture of diethyl ether-hexane (4:1, v/v) at low temperature. The precipitated samples were dried at room temperature under reduced pressure to constant weight.

The experimental conditions are summarized in Table 1. 2-acetyl-5-methacrylamidosalicylic acid and 2-hydroxyethyl methacrylate are referred to compound 5 and HEMA in Table 1, respectively.

Number average molecular weight, which is referred to Mn, and weight average molecular weight, which is referred to Mw were measured by gel permeation chromatography. The result is summarized in Table 2.

TABLE 1

|  |  | compound 4 |  | HEMA |  | AIBN | DMF |
|---|---|---|---|---|---|---|---|
| Ex. |  | (g) | (mol. %) | (g) | (mol. %) | (g) | (g) |
| 12 | 5 | 0.65 | 4.97 | 6.18 | 95.03 | 0.082 | 63 |
| 13 | 10 | 1.0 | 9.90 | 4.5 | 90.05 | 0.063 | 49.5 |

TABLE 1-continued

| Ex. | compound 4 (g) | (mol. %) | HEMA (g) | (mol. %) | AIBN (g) | DMF (g) |
|---|---|---|---|---|---|---|
| 14 | 20 | 3.5 | 19.82 | 7 | 80.18 | 0.11 | 94.5 |
| 15 | 100 | 1.5 | 100 | 0 | 0 | 0.02 | 21 |

TABLE 2

| Ex. | yield (%) | elemental analysis C | H | N | exp. ratio (wt. %) | molecular weight × 10⁴ Mn | Mw | Mw/Mn |
|---|---|---|---|---|---|---|---|---|
| 12 | 72.2 | 55.57 | 7.65 | 0.31 | 6.00 | 3.07 | 8.58 | 2.8 |
| 13 | 45.1 | 55.76 | 7.46 | 0.52 | 10.1 | 4.98 | 10.05 | 2.02 |
| 14 | 64.1 | 51.98 | 7.11 | 1.18 | 22.8 | 4.22 | 9.18 | 2.17 |
| 15 | 66.7 | 59.31 | 5.01 | 5.17 | 100 | 2.01 | 4.71 | 2.34 |

COMPARATIVE EXAMPLES 1 AND 2

5-methacrylamidosalicylic acid that was obtained in the step (1) in Example 3 was polymerized with 2-hydroxyethyl methacrylate in the same procedures as Examples 12–14 to give a copolymer. 5-methacrylamidosalicylic acid is referred to compound 5 in Table 3.

COMPARATIVE EXAMPLE 3

5-methacrylamidosalicylic acid was polymerized in the same procedures as Example 15 to give a homopolymer.

BIOCOMPATIBLE TEST

Each of the polymer materials was coated onto an inner surface of a test tube, and exposed to the fresh blood from goat. Lee-White test showed the coagulation time and occurrence of hemolysis. The result is summarized in Table 3.

The polymers of Examples 12, 14 and 15 contain 2-acetyl-5-methacrylamidosalicylic acid moiety containing the acetyl group whereas the polymers of Comparative Examples 1, 2 and 3 contain 5-methacrylamidosalicylic acid moiety free of the acetyl group. Coagulation times increase in Examples 12, 14 and 15 compared to Comparative Examples 1, 2, and 3, respectively. The result shows that the presence of the acetyl group in the salicylic acid moiety increases the coagulation time.

TABLE 3

Result of Biocompatible Test

| Run No. | sample | coagulation time (min.) | hemolysis |
|---|---|---|---|
| Examples | | | |
| 12 | copolymer of 5% of compound 5 and 95% of HEMA | 32.0 | negative |
| 14 | copolymer of 20% of compound 5 and 80% of HEMA | 46.3 | negative |
| 15 | homopolymer of compound 5 | 59.3 | negative |
| Comparative Examples | | | |
| 1 | copolymer of 5% of compound 6 and 95% of HEMA | 17.2 | negative |
| 2 | copolymer of 20% of compound 6 and 80% of HEMA | 18.6 | negative |
| 3 | homopolymer of compound 6 | 21.3 | negative |

TABLE 3-continued

Result of Biocompatible Test

| Run No. | sample | coagulation time (min.) | hemolysis |
|---|---|---|---|
| 4 | segmented polyurethane | 22.7 | negative |
| 5 | polyvinyl chloride having medical grade | 18.7 | negative |
| 6 | glass tube | 16.5 | positive |

What is claimed is:

1. A monomer, or a salt thereof, of the formula:

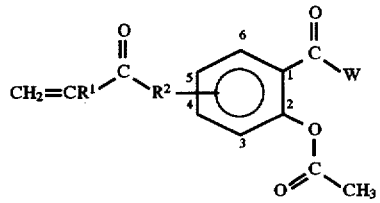

wherein $R^1$ is hydrogen or methyl;
$R^2$ is —O— or —NH—; and
W is hydroxy, lower alkoxy, aryloxy, aralkyloxy, acyloxy and —N($R^3$)($R^4$) wherein $R^3$ and $R^4$ are each hydrogen or lower alkyl.

2. A monomer, or a salt thereof, according to claim 1, wherein $R^2$ is —NH—.

3. A monomer, or a salt thereof, according to claim 2, wherein W is hydroxy, $C_{1-6}$ lower alkoxy, phenoxy or amino.

4. A monomer, or a salt thereof, according to claim 1, claim 1 wherein $R^2$ is —O—.

5. A monomer, or a salt thereof, according to claim 4, wherein W is hydroxy, $C_{1-6}$ lower alkoxy, phenoxy or amino.

6. A polymer, or a salt, thereof comprising monomeric units of the formula:

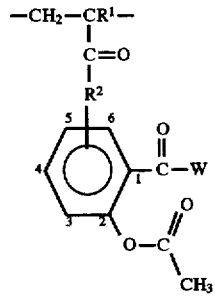

wherein $R^1$ is hydrogen or methyl;
$R^2$ is —O— or —NH—; and
W is hydroxy, lower alkoxy, aryloxy, aralkyloxy, acyloxy and —N($R^3$)($R^4$) wherein $R^3$ and $R^4$ are each hydrogen or lower alkyl.

7. A polymer, or a salt thereof, according to claim 6, wherein $R^2$ is —NH—.

8. A polymer, or a salt thereof, according to claim 6, wherein W is hydroxy, $C_1$–$C_6$ lower alkoxy, phenoxy or amino.

9. A polymer, or a salt thereof, according to claim 6, wherein $R^2$ is —O—.

10. A polymer, or a salt thereof, according to claim 1, wherein W is hydroxy, $C_1$–$C_6$ lower alkoxy, phenoxy or amino.

11. A polymer, or a salt thereof, according to claim 6, further comprising monomeric units of the formula:

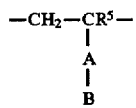

wherein $R^5$ is hydrogen, methyl or halogen;

wherein A designates a single bond, $C_{1-3}$ alkylene, —O—, —C(O)—O—, —O—C(O)—, —N($R^6$)—C(O)— or —C(O)—N($R^6$)—, wherein $R^6$ is hydrogen, lower alkyl, amino lower alkyl or alkylamino lower alkyl; and B is hydrogen, halogen, alkyl, alkenyl, alkynyl, cycloalkyl or aryl.

12. A copolymer according to claim 11, wherein $R^5$ is hydrogen or methyl; and A is —C(O)—NH—.

13. A medical article consisting essentially of the polymer of claim 6.

14. A medical article consisting essentially of the polymer of claim 7.

15. A medical article consisting essentially of the polymer of claim 8.

16. A medical article consisting essentially of the polymer of claim 9.

17. A medical article consisting essentially of the polymer of claim 10.

18. A medical article consisting essentially of the copolymer of claim 11.

19. A medical article consisting essentially of the copolymer of claim 12.

* * * * *